(12) United States Patent
Al-Sowayan

(10) Patent No.: US 11,744,857 B2
(45) Date of Patent: Sep. 5, 2023

(54) METHOD FOR TISSUE REGENERATION USING CANCER CELL-DERIVED EXOSOMES

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Batla S. Al-Sowayan, Al Izdhar (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 1029 days.

(21) Appl. No.: 16/390,416

(22) Filed: Apr. 22, 2019

(65) Prior Publication Data
US 2020/0330512 A1    Oct. 22, 2020

(51) Int. Cl.
| | | |
|---|---|---|
| *A61K 35/13* | (2015.01) | |
| *A61K 35/28* | (2015.01) | |
| *A61K 35/44* | (2015.01) | |
| *A61K 35/34* | (2015.01) | |
| *A61K 9/127* | (2006.01) | |
| *A61L 27/38* | (2006.01) | |
| *A61K 9/00* | (2006.01) | |
| *C12N 5/09* | (2010.01) | |
| *A61P 9/00* | (2006.01) | |

(52) U.S. Cl.
CPC ............ *A61K 35/13* (2013.01); *A61K 9/0019* (2013.01); *A61K 9/127* (2013.01); *A61K 35/28* (2013.01); *A61K 35/34* (2013.01); *A61K 35/44* (2013.01); *A61L 27/3804* (2013.01); *A61L 27/3834* (2013.01); *A61L 27/3839* (2013.01); *A61L 27/3895* (2013.01); *A61P 9/00* (2018.01); *C12N 5/0693* (2013.01); *A61L 2430/20* (2013.01); *C12N 2500/90* (2013.01)

(58) Field of Classification Search
CPC ...... A61K 35/13; A61K 9/0019; A61K 9/127; A61K 35/28; A61K 35/34; A61K 35/44; A61K 35/12; A61L 27/3804; A61L 27/3834; A61L 27/3839; A61L 27/3895; A61L 2430/20; A61P 9/00; C12N 5/0693; C12N 2500/90; C12N 2310/141; C12N 15/113

See application file for complete search history.

(56) References Cited

U.S. PATENT DOCUMENTS 9,579,287 B2    2/2017    Montero-Menei et al.

OTHER PUBLICATIONS

Anna Gutkin, et al., "Tumor cells derived exosomes contain hTERT mRNA and transform nonmalignant fibroblasts into telomerase positive cells", Oncotarget, vol. 7, No. 37, Jul. 2, 2016, pp. 59173-59188.

Jason Webber, et al., "Cancer Exosomes Trigger Fibroblast to Myofibroblast Differentiation", Microenvironment and Immunology, Cancer Research, vol. 70, No. 23, Dec. 1, 2010, pp. 9621-9630.

Katie Meehan, et al., "The contribution of tumour-derived exosomes to the hallmarks of cancer", Critical Reviews in Clinical Laboratory Sciences, 2015, pp. 1-11.

*Primary Examiner* — Robert S Cabral
(74) *Attorney, Agent, or Firm* — Oblon, McClelland, Maier & Neustadt, L.L.P.

(57) ABSTRACT

The invention pertains to a method for temporarily conferring advantageous cancer cell phenotypes, such as a higher proliferation rate, resistance to apoptosis and cell death, and resistance to endogenous factors that inhibit cell growth, on non-cancer cells that help repair and regenerate damaged tissues.

15 Claims, No Drawings

METHOD FOR TISSUE REGENERATION USING CANCER CELL-DERIVED EXOSOMES

BACKGROUND OF THE INVENTION

Field of the Invention

Regenerative medicine and cellular biology embodied in a method of using cancer cell-derived exosomes to regenerate damaged tissue or other tissue in need of regeneration.

Description of Related Art

This "background" description provides a general context helpful in understanding, the invention. The work of the presently named inventor to the extent that it is described in this section, as well as aspects of the description which may not otherwise qualify as prior art at the time of filing, are neither expressly or impliedly admitted as prior art against the present invention. Subject matter described within the background section may provide descriptive support for elements of the invention and is incorporated by reference to the corresponding publications cited therein.

Myocardial infarction (MI) is a major contributor to global disease burden. MI, commonly known as a heart attack, occurs when there is a prolonged lack of oxygen supply to the heart. Cardiomyocytes make up the atria (the chambers in which blood enters the heart) and the ventricles (the chambers where blood is collected and pumped out of the heart). These cells must be able to shorten and lengthen their fibers and the fibers must be flexible enough to stretch. These functions are critical to achieve proper form during the beating of the heart. Like any muscle of the body, the heart requires a constant supply of oxygen.

If a coronary artery or one of its branches becomes blocked, the portion of the heart that is supplied by the blocked vessel will become deprived of oxygen. The lack of oxygen will initiate an ischemic cascade where ischemia or cell starvation due to the lack of oxygen causes myocardial cells, the main constituent of the heart, to die. The dead cells are replaced by a collagen scar that lacks the functional properties of cardiomyocytes, causing an irreversible damage to the heart; Abbate A, Biondi-Zoccai G G, Baldi A., Pathophysiologic role of myocardial apoptosis in post-infarction left ventricular remodeling. J Cell Physiol. 2002; 193(2): 145-53.

Cardiac dysfunction due to MI damage, accounts for the majority of cardiovascular disease-associated deaths worldwide; Moran A E, Forouzanfar M H, Roth G A, Mensah G A, Ezzati M, Flaxman A, et al. The global burden of ischemic heart disease in 1990 and 2010: the Global Burden of Disease 2010 study. Circulation. 2014; 129(14): 1493-501.

Currently, the main MI management strategy is to limit and prevent further damage to the myocardial tissue. This is done through the administration of a group of drugs that initiate reperfusion and reduce physical exertion on the heart; Maxwell S., Emergency management of acute myocardial infarction. Br. J. Clin. Pharmacol. 1999; 48(3): 284-98. Even though the drug approach is relatively effective, it still has its limitations in controlling MI manifestations with high mortality rates within a year following MI onset; Jemberg T, Hasvold P, Henriksson M, Hjelm H, Thuresson M, Janzon M. Cardiovascular risk in post-myocardial infarction patients: nationwide real world data demonstrate the importance of a long-term perspective. Eur. Heart J. 2015; 36(19): 1163-70. Therefore, researchers in regenerative medicine have aimed to not only limit ischemia-caused damage, but also to regenerate the affected myocardial tissue via cellular-based therapy.

The mesenchymal stem cell (MSC) is one of the most investigated cell types in regenerative medicine. This is mainly due to its vast differentiation potential, its immunomodulatory effects, and its ability to revive endogenous stem cell niches; Karantalis V, Hare J M. Use of mesenchymal stem cells for therapy of cardiac disease. Circ Res. 2015; 116(8): 1413-30; Zhang, H, Xiang M, Meng D, Sun N, Chen S. Inhibition of Myocardial Ischemia/Reperfusion Injury by Exosomes Secreted from Mesenchymal Stem Cells. Stem Cells Int. 2016; 2016: 4328362.

In preclinical and early phase clinical trials, the administration of MSCs following MI helped reduce the ischemic manifestations and improved recovery of cardiac tissue; Hare J M, Fishman J E, Gerstenblith G, DiFede Velazquez D L, Zambrano J P, Suncion V Y, et al. Comparison of allogeneic vs autologous bone marrow-derived mesenchymal stem cells delivered by transendocardial injection in patients with ischemic cardiomyopathy: the POSEIDON randomized trial. JAMA. 2012; 308(22): 2369-79; Houtgraaf J H, den Dekker W K, van Dalen B M, Springeling T, de Jong R, van Geuns R J, et al. First experience in humans using adipose tissue-derived regenerative cells in the treatment of patients with ST-segment elevation myocardial infarction. J Am Coll Cardiol. 2012; 59(5): 539-40. It has been proposed that MSCs induce angiogenesis and exert cardio-protective effects mainly through the release of a paracrine factor called an exosome.

Exosomes are spherical-shaped particles enclosed by a phospholipid bilayer. According to the International Society for Extracellular Vesicles, extracellular vesicles (EVs) are classified into exosomes, ectosomes, microvesicle panicles, and apoptotic bodies; Lotvall J, Hill A F, Hochberg F, Buzas E I, Di Vizio D, Gardiner C, et al. Minimal experimental requirements for definition of extracellular vesicles and their functions: a position statement from the International Society for Extracellular Vesicles. J, Extracell. Vesicles, 2014; 3: 26913. The distinction between these EVs is based on their subcellular origin, protein composition, size, morphology and density.

Exosomes originate from a subcellular compartment called an endosome. When the cell content is sorted, endocyytic vesicles fuse with early endosomes releasing their proteins/lipids content. Recyclable content is taken into a recycling endosome and the early endosome becomes a late endosome or multivesicular body (MVB). Content of the MVB will be packed into small vesicles called intraluminal vesicles (ILVs): Akers J C, Gonda D, Kim R, Carter B S, Chen C C. Biogenesis of extracellular vesicles (EV): exosomes, microvesicles, retrovirus-like vesicles, and apoptotic bodies. J Neurooncol. 2013; 113(1): 1-11; Record M. Carayon K, Poirot M, Silvente-Poirot S. Exosomes as new vesicular lipid transporters involved in cell-cell communication and various pathophysiologies. Biochim Biophys Acta. 2014; 1841(1): 108-20. Depending on their content, ILVs are sent for either degradation or exocytosis. ILVs released into the extracellular space constitute what is called exosomes; Keller S. Sanderson M P, Stoeck A, Altevogt P. Exosomes: from biogenesis and secretion to biological function. Immunol Lett. 2006; 107(2): 102-8; Mathivanan S, Ji H, Simpson R J. Exosomes: extracellular organelles important in intercellular communication. J Proteomics. 2010, 73(10): 1907-20.).

Exosomes may be characterized based on their protein composition. Mathivanan and Simpson have created "ExoCarta", an exosome database (www.exocarta.org) that provides a list of the most commonly identified proteins in exosomes based on submission of independent exosome examinations; Mathivanan S, Simpson R J. ExoCarta: A compendium of exosomal proteins and RNA. Proteomics. 2009; 9(21): 4997-5000.

One or more of these proteins or miRNAs can be used as a marker to characterize an exosome. For example, in a study of human bone marrow MSC (BMMSC)-derived exosomes, purified exosomes where detected by using CD9 and CD81 as protein markers, in addition to shape and size assessment; Zhu W, Huang L, Li Y, Zhang X, Gu J, Van V, et al. Exosomes derived from human bone marrow mesenchymal stem cells promote tumor growth in vivo. Cancer Lett. 2012; 315(1): 28-37.

Exosomes may also contain distinguishing proteins that reflect their cellular origin. For example, unlike other exosomes, immune cell-derived exosomes are enriched in major histocompatibility complex II protein; Marcus M E, Leonard J N. FedExosomes: Engineering Therapeutic Biological Nanoparticles that Truly Deliver. Pharmaceuticals (Basel). 2013: 6(5): 659-80.

Another example, in maternal circulation, placenta-derived exosomes can be distinguished by the presence of placental alkaline phosphate protein; Mitchell M D, Peiris H N, Kobayashi M, Koh Y Q, Duncombe G, Illanes S E, et al. Placental exosomes in normal and complicated pregnancy. Am J Obstet Gynecol. 2015; 213(4 Suppl): S173-81.

Exosomes have round, cup-shaped morphology and are generally found to be 50 to 100 nm in diameter by transmission electron microscopy; Nazarov I, Lee J W, Soupene E, Etemad S, Knapik D, Green W, et al. Multipotent stromal stem cells from human placenta demonstrate high therapeutic potential. Stem Cells Transl Med. 2012; 1(5): 359-72; van der Pol E, Boing A N, Harrison P Stark A, Nieuwland R. Classification, functions, and clinical relevance of extracellular vesicles. Pharmacol Rev. 2012; 64(3): 676-705. However, some researchers accept a wider range that goes down to 30 nm; Hu G, Drescher K M, Chen X M. Exosomal miRNAs: Biological Properties and Therapeutic Potential. Front Genet. 2012.; 3: 56; Sun D Zhuang X, Zhang S, Deng Z B, Grizzle W, Miller D, et al. Exosomes are endogenous nanoparticles that can deliver biological information between cells. Adv Drug Deliv Rev. 2013; 65(3): 342-7.

It is important to note that the diameter of an exosome is largely dependent on the technique used to measure it. For example, the diameter of MSC-derived exosomes was around 30-50 nm when measured by scanning electron microscope (SEM). When the same sample was measured using dynamic light scattering (DLS), the diameter was 208 nm: while nanoparticle tracking analysis (NTA) indicated a diameter of 110 nm; Sokolova V. Ludwig A K, Hornung S. Rotan O, Horn P A, Epple M, et al. Characterisation of exosomes derived from human cells by nanoparticle tracking analysis and scanning electron microscopy. Colloids Surf B Biointerfaces. 2011; 87(1): 146-50.

Exosomes have a characteristic density of 1.13-1.19 g/ml in sucrose which permits them to be separated from other cellular components having different densities by various exosome harvesting protocols. The protocols include differential centrifugation and/or filtration to remove dead cells and debris, followed by ultracentrifugation coupled with a sucrose density gradient; Chen L, Wang Y, Pan Y, Zhang L, Shen C, Qin G, et al. Cardiac progenitor-derived exosomes protect ischemic myocardium from acute ischemia/reperfusion injury. Biochem Biophys Res Commun. 2013; 431(3): 566-71; Xin H, Li Y, Buller B, Katakowski M, Zhang Y. Wang X, et al. Exosome-mediated transfer of miR-133b from multipotent mesenchymal stromal cells to neural cells contributes to neurite outgrowth. Stem Cells. 2012; 30(7): 1556-64. However, the ultracentrifugation methods are usually quite laborious and time consuming. Hence, other exosome harvesting techniques are being developed based on different principles. For example, size-based exosome isolation which utilizes sequential filtration or size exclusion chromatography; Li P, Kaslan M, Lee S H, Yao J, Gao Z. Progress in Exosome Isolation Techniques. Theranostics. 2017; 7(3): 789-804 Immune-based isolation, where exosomes are collected via capture antibodies. Whereas most commercial kits available for exosome isolation are based on the precipitation principle; Katakowski M, Buller B, Zheng Lu Y, Rogers T, Osobamiro O, et al. Exosomes from marrow stromal cells expressing miR-146b inhibit glioma growth. Cancer Lett. 2013; 30(1): 201-4; Zhang Y, Chopp M, Meng Y, Katakowski M, Xin H, Mahmood A, et al. Effect of exosomes derived from multipluripotent mesenchymal stromal cells on functional recovery and neurovascular plasticity in rats after traumatic brain injury. J Neurosurg. 2015; 122(4): 856-67.

In view of the limitations of conventional regenerative treatments, such as those for tissue damage or specifically for damage caused by myocardial infarction, and a need for, a safer, faster and more efficient method for repair or regeneration of tissues, the inventor investigated ways to repair or regenerate tissues such as those damaged by myocardial infarction using exosomes derived from cancer cells.

BRIEF SUMMARY OF THE INVENTION

In one aspect, the invention is directed to a method for using exosomes obtained from cancer cells to enhance the properties of normal cells that participate in repair and regeneration of damaged tissue. Exosomes are released by both normal and cancer cells as a form of intercellular communication based on the protein and miRNA content of an exosome. The inventor have recognized that cancer cell-derived exosomal content, which induces proliferation, death resistance and growth suppressors evasion, replicative immortality, angiogenesis, invasion and metastasis in recipient cells, can be advantageously used to temporarily enhance these properties in normal cells that repair and regenerate damaged tissue. In other words, these properties which promote the aggressiveness of cancer cells can be transferred in an "epigenetically temporary manner" to allow normal cells to more efficiently regenerate damaged tissue. Placement of cancer cell-derived exosomes in a damaged tissue microenvironment, such as damaged cardiac tissue, allows damaged cardiomyocytes and damaged microvascular cells to take these exosomes and their protein and miRNA containing cargo and to undergo a temporary tumorigenic transformation (i.e., activation of telomerase, induced proliferation and angiogenesis and other hallmarks of cancer cells) thus enhancing the ability of the damaged tissue to regenerate or repair itself. The method disclosed herein can be used to treat tissue damage caused by myocardial infarction as Tell as other types of tissue damage.

As disclosed herein the inventor sought to apply these properties of cancer cells to cells of damaged tissue by producing exosomes from cancer cells and treating on-cancer cells with these exosomes, thus conferring properties of cancer cells to these cells in the service of repair and regeneration of the damaged tissue.

The invention also contemplates compositions containing exosomes derived from cancer cells, including mixtures of exosomes and cells involved in repair, useful in this method of treatment.

The foregoing paragraphs have been provided by way of general introduction, and are not intended to limit the scope of the following claims. The described embodiments, together with further advantages, will be best understood by reference teethe following detailed description.

DETAILED DESCRIPTION OF THE INVENTION

Cancer cell-derived exosomes have a set of distinguished proteins and miRNAs These proteins and miRNAs are responsible for cancer cell-cell communication, and thus, cancer propagation. A number of distinctive miRNAs encapsulated in cancer cell-derived exosomes were identified in previous literature, with each activating a certain cellular pathway. For example, hTERT (and hTERT miRNA) was identified within the cancer cell-derived exosomes, which can activate the telomere region in recipient cells.

This method may be practiced on all tissues, including the cardiovascular tissues. Exosomes from non-cancerous cells, like stem cells and cardio progenitor cells (CPC), are being investigated and are showing promising results. However, the inventors consider that the distinguished and "abnormal" combination of proteins and miRNAs, such as those of hTERT, within the cancer cell-derived exosomes that are responsible for strenuous cancer cells propagation will have a superior effect on tissue regeneration.

The invention is directed to new methods for treating damaged tissue using exosomes from cancer cells. Cancer cells exhibit a number of properties or "hallmarks of cancer" that differentiate them from normal cells including replicative immortality, higher rates of proliferation, resistance to cellular death and apoptosis, evasion of suppressive effects of endogenous growth regulators, ability to induce angiogenesis, and the ability to invade normal tissues and metastasize. The inventor considers that unlike exosomes from non-cancerous cells or stem cells or cardioprogenitor cells (CPCs), that cancer cell derived exosomes may be distinguishable based on an abnormal (compared to non-cancer cells) combination of protein and The inventor further considered that these abnormal contents of cancer cell derived exosomes are responsible for strenuous cancer cell propagation, cellular proliferation, and replicative immortality and resisting cell death, evading growth suppressors, and inducing angiogenesis and invasion and thus would have superior effects on initiating, accelerating, or maintaining tissue regeneration on many different types of tissues in need of regeneration. The inventor also considered that unlike these properties when manifested by cancer cells, activation of normal, non-cancerous cells by cancer cell derived exosomes would confer these properties in a temporary way, thus avoiding dangers associated with unchecked cellular growth. As a model of this ability of cancer cell derived exosomes to enhance regeneration of damaged tissue, damage caused by myocardial infarction vas proposed as a useful model. This model involves study of the ability of cancer cell derived exosomes to repair or regenerate cardiovascular cells damaged by myocardial infarction.

Embodiments of the invention include but are not limited to the following.

One embodiment of the invention is directed to a method for repairing or regenerating tissue damaged by myocardial infarction in a subject including administering to a subject in need thereof an effective amount of cancer cell-derived exosomes.

"Subject" and "patient" as used herein interchangeably refers to any vertebrate, including, but not limited to, a mammal (e.g., human, non-human primate, cow, pig, camel, llama, horse, goat, rabbit, sheep, hamsters, guinea pig, cat, dog, rat, and mouse. The subject may be a human or a non-human. The subject or patient may be undergoing other forms of treatment. A subject may be male or female, young or old, for example, <1, 2, 3, 4, 5, 10, 15, 20, 25, 30, 35, 40, 45, 50, 55, 60, 65, 70, 75, 80, 85, 90, 95, 100 or >100 years old or any intermediate value within this range.

The term "damage caused by myocardial infarction" as used herein refers to any injury to the heart, vasculature, or surrounding tissues resulting from myocardial infarction. In some instances, this tissue will be part of a zone of ischemia containing cells that can regain function after the onset of the myocardial infarction; a part of an area of injury containing cells that can regain function after the onset of the myocardial infarction; an area of infarction containing dead cells or necrotic tissue or a tissue that exhibits myofibrillar degeneration and/or diffuse inflammatory processes; or an area of incomplete or complete scar formation, such as formation of a collagen scar.

A subject may have had a myocardial infarction less than 6, 12, 18, or 24 hours ago or a myocardial infarction 1, 2, 3, 4, 5, 6, 7, 8, 9, 10, 11, 12, 13, 14, 28 or >28 days ago. Damage caused by myocardial infarction may be present in tissue of the left or right vertical or left or right atrium as well as other portions of the heart or its vasculature.

In other embodiments, a subject may be suffering from damage to or insufficient amounts of, another tissue such as air epithelial (e.g., simple epithelium, stratified epithelium, pseudostratified columnar epithelium, glandular epithelium), connective (e.g., loose or dense connective tissues or cartilages), muscular (e.g., skeletal, cardiac or smooth muscle) or nervous tissue (e.g., neurons, neuroglial). For example, cancer cell-derived exosomes can be used to confer the advantageous properties of cancer cells on chondrocytes or other regenerative cells in the synovium as a means to treat arthritis, wounds, such as puncture wounds, incisions, lacerations, avulsions, amputations, and abrasions; or burns including cold burns, friction burns, thermal burns, radiation burns including sunburn, chemical burns or electrical burns. The method may be used to treat first, second or third degree burns by enhancing repair or regeneration of damaged tissue. The cancer cell-derived exosomes of the invention may also be used to promote repair, healing, or rejuvenation of damage caused by autoimmune diseases, neurological diseases including stroke, cardiovascular diseases, such as asthma, COPD, congestive heart failure, to treat sports related injuries including grade 1 or 2 tears, overuse injuries, orthopedic sports related injury and to accelerate post-operative healing. Other uses include acceleration of healing after a cosmetic procedure including plastic surgery or dermabrasion or for treatment of acne r other skin lesions, or to promote hair regrowth or to accelerate healing after hair transplantation.

In still other embodiments, the cancer cell-derived exosomes can be used ex vivo or in vitro to promote the growth of cells in scaffolds used to grow artificial organs. Cancer cell-derived exosomes may be used for the regeneration and growth acceleration of any somatic tissue type both in vivo and in vitro. In some embodiments, cellular growth supplements are included in such methods.

The cancer-cell derived exosomes ay be administered by any mode that permits them to promote healing of damaged tissue, such as epithelial tissue, connective tissue, muscle tissue and nervous tissue. Damaged tissue may result from soft tissue injuries (e.g., damage to muscle ligaments, tendons, menisci, wounds and burns of the skin or damaged joints, or endothelium or other arterial, venous, of lymphatic tissues), hard tissue injuries (e.g., bone or teeth), or injuries to nerve tissue. In some embodiments, the tissue damage is caused by myocardial infarction).

Typically, the exosomes are administered in vivo, although in some embodiments, the cancer-cell derived exosomes may be contacted with target cells ex vivo or in vitro. Preferably, the exosomes are administered, direct injection or implanted on a sheet, into or around tissue damaged by myocardial infarction, including into or around tissue damaged by ischemic, necrotic tissue, or scar tissue. In some embodiments, the cancer-cell derived exosomes are administered subcutaneously. In other embodiments, the exosomes are administered intravenously.

Any dosage of cancer cell-derived exosomes that is effective to promote repair, healing or regeneration of tissue damaged by myocardial infarction or other damaged tissue may be used. A dosage of cancer cell-derived exosomes ranging containing <0.01, 0.01, 0.02, 0.05, 0.1 0.2, 0.5, 1, 2, 5, 10, 10, 20, 30, 40, 50, 60, 70, 80, 90, 100, 200, 300, 400, 500, 600, 700, 800, 900, 1,000, 2,000, 3,000 or >3,000 µg of exosomal protein per kilogram of body weight of a subject is used. This range includes all intermediate values and subranges. Dosages may be modified based on mode of administration, for example, a larger dosage may be administered intravenously than a dosage administered in situ to damaged cardiac tissue or to a dosage administered topically.

In some embodiments of the invention exosomes are injected directly into a damage tissue, e.g., into ate ischemic heart. In other embodiments, the exosomes may be fixed on a scaffold or a gel then placed on the damaged tissue to prevent the exosome from being flushed away from the injured tissue, e.g., into the circulation.

In some embodiments exosomes may be admixed with other cellular growth factors, nutrients, or cellular proteins. These include, but are not limited to vascular endothelial growth factor (VEGF), fibroblast growth factor (FGF), hepatocyte growth factor, platelet-derived growth factor (PDGF-BB), protein thymosin β4, IL-11, IL-33, and others. These mixtures can be used to increase the effectiveness of the exosomes or prolong shelf-life of exosome-containing preparations. The term "administration" or "administering" as used herein describes a process by which the disclosed cancer cell derived exosome compositions may be delivered to a subject. Administration will often depend upon the amount of composition administered, the number of doses, and duration of treatment. Multiple doses of the composition may be administered. The frequency and duration of administration of the composition can vary, depending on any of a variety of factors, including patient response. The exosome compositions may be administered to the subject by any suitable route. For example, the compositions may be administered parenterally, e.g., by intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, or epidural injection, by infusion, by electroporation, or by co-administration as a component of any medical device or object to be inserted (temporarily or permanently) into a subject. For example, the exosome compositions may be administered intranasally.

A "therapeutically effective amount," or "effective dosage" or "effective amount" as used interchangeably herein unless otherwise defined, means a dosage of a drug effective for periods of time necessary, to achieve the desired therapeutic result such as healing, repair or regeneration of damaged, scarred, or necrotic heart tissue. A suitable single dose size is a dose that is capable of inducing or sustaining healing, repair or regeneration in a subject when administered one or more times over a suitable time period. An effective dosage may be determined by a person skilled in the art and may vary according to factors such as the disease state, age, sex, and weight of the individual, and the ability of the drug to elicit a desired response in the individual. Therapeutically effective amounts for the disclosed exosome compositions can be readily determined by those of ordinary skill in the art. A therapeutically effective amount may be administered in one or more administrations (e.g., the cancer cell derived exosome composition may be given as a preventative treatment or therapeutically at any stage of injury due to myocardial infarction or prophylactically in patients at risk of a myocardial infarction, such as those with cardiovascular disease, before or after symptoms, and the like), applications or dosages and are not limited to a particular formulation, combination or administration route. It is within the scope of the present disclosure that the disclosed exosome compositions may be administered at various times during the course of treatment of the subject. The times of administration and dosages used will depend on several factors, such as the disease state, age, sex, and weight of the individual, and the ability of the composition to elicit a desired response in the individual. Administration may be adjusted according to individual need and professional judgment of a person administrating or supervising the administration of the cancer cell-derived exosomes, regenerative cells, or drugs used in the present invention.

Administration of the cancer cell-derived exosomes and other active ingredients may be as a single dose or multiple doses over a period of time. The exosome composition may be administered to the patient at any frequency necessary to achieve the desired therapeutic effect. For example, the exosome composition may be administered continuously, once to several times every month, every two weeks, every week, or every day. Administration of the exosome composition may be repeated until the desired therapeutic effect has been achieved. For example, the exosome composition may be administered once to several times over the course of 1 day, 3 days, 5 days, 1, 2, or 3 weeks, or 1, 2, 3, 4, 5, 6, 7, 8, 9, 10, 11 or 12 months or more than 12 months.

An amount of the cancer cell-derived exosome composition to be administered may depend on a variety of factors, such as the route of administration and the seriousness of the condition, and should be decided according to the judgment of the practitioner and each patient's circumstances. The exosome composition may be administered to a subject in any amount suitable for the prevention or treatment of damage caused by myocardial infarction. An effective amount of the exosome composition may cause a partial improvement or a complete elimination of symptoms due to damage associated with myocardial infarction. Treatment may include promoting regeneration of cardiomyocytes or endothelial tissue following myocardial infarction or reduction in an amount of scar tissue, such as collagen scar tissue. Treatment may include enhancing survival cardiomyocytes or endothelial tissue exposed to ischemia or deprivation of oxygen. It may include decreasing the area or volume of scar tissue after myocardial infarction.

Suitable dosage ranges of the cancer cell-derived exosomes include from about 0.001 μg exosome/kg body weight to about 100 mg/kg, about 0.01 μg/kg to about 90 mg/kg, about 0.1 μg/kg to about 80 mg/kg, about 1 μg/kg about 70 mg/kg, about 10 g/kg to about 60 mg/kg, about 0.1 mg/kg to about 50 mg/kg, about 0.5 mg/kg to about 25 mg/kg, about 1 mg/kg to about 10 mg/kg, or about 2.5 mg/kg to about 5 mg/kg. For example, suitable dosage ranges of the exosome composition include about 0.001 μg/kg, about 0.01 μg/kg, about 0.1 μg/k, about 1.0 μg/kg, about 10 μg/kg, about 0.1 mg/kg, about 0.5 mg/kg, about 1 mg/kg, about 2.5 mg/kg, about 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg, about 90 mg/kg, or about 100 mg/kg. In vitro or in vivo assays may optionally be employed to help identify optimal dosage ranges. Effective doses may be extrapolated from dose-response curves derived from in vitro or animal model test systems.

In some embodiments, the exosomes are administered into stem cells or cardiomyocytes ex vivo or in vitro prior to administering these exosome-contacted cells to a subject. Cancer cell-derived exosomes used in this method may be obtained from cancer cell explains cultured ex vivo or from cancer cell lines cultured in vitro. Typically cancer cell derived exosomes will range in size from about 30, 40, 50, 60, 70, 80, 90, 100, 120, 150, 200, 220, 250, 300 or >300 nm, preferably from about 50 to 100 nm, as measured by TEM and a density ranging from about 1, 1.1, 1.2, 1.3, 1.4 to 1.5 g/ml in sucrose, preferably a density of about 1.13-1.19 g/ml in sucrose.

Exosomes may be isolated from cancer cells by techniques known in the art, including those described herein, and preferably by size exclusion chromatography (SEC). Preferably, exosomes are isolated from 10, 20, 30, 40, 50, 60, 70 80, 90, 95, 99 or >99 wt % of extra-exosomal nucleic acids, proteins and other cellular components of the cancer cells from which they are derived. The term "extra-episomal" component refers to components not contained within the exosome or embedded in its membrane. Such extra-episomal components can include genomic DNA of a cancer cell, coding RNA (e.g., mRNA) of a cancer cell not contained inside the exosome or not associated with its membrane, non-coding RNA (e.g., miRNA) not contained inside the exosomes or not associated with its membrane, cellular or serum proteins not contained inside the exosomes or not associated with exosomal membrane.

Cancer cell derived exosomes may be isolated from cancer cells, especially from those exhibiting the so-called hallmarks of cancer which include transformation or mutation that enables cellular proliferation of the cancer cell, permits it to resist cell death or apoptosis, confers replicative immortality, permits the cell to induce angiogenesis, permits the cancer cell to evade growth suppressors, and which otherwise stimulates invasion and metastasis of the cancer cell. As recognized by the inventor, these traits, which are detrimental in cancer cells, are useful when conferred on cells involved in or used to repair damage caused by myocardial infarction.

Cancer cell derived exosomes may have a density ranging from about 1.1-1.25 g/ml in sucrose, preferably from 1.13-1.19 g/ml in sucrose. Cancer cell-derived exosomes may have an average diameter measured by TEM of about 30 to 200 nm, preferably from about 50 to 100 nm. An exosome may contain at least 5,000, 10,000, 20,000, 30,000 or 40,000 protein molecules and contain coding (e.g., mRNA) or non-coding RNA (e.g., pre-miRNA or mature miRNA). Some exosomes may carry double stranded DNA. The content of exosomes may differ depending on the nature of the parent cell. Consequently, exosomes from cancer cells derived from a tissue similar to that of a normal tissue in need of regeneration may be used.

In some embodiments, the cancer cells from which the exosomes are derived are breast cancer cells, colorectal cells or cancers of mesenchymal origin. Other types of cancer cells useful in the invention include those from cancer of the blood, brain, bladder, lung, cervix, ovary, colon, rectum, pancreas, skin, prostate gland, stomach, breast, liver, spleen, kidney, head, neck, testicle, bone, bone marrow, thyroid gland or central nervous system. In some embodiments, cancer cells used to source exosomes are sarcomas (soft tissue cancer) or from transformed tissues similar to heart tissue, e.g., from a primary heart cancer. In other embodiments, cancer cells used to isolate exosomes are metastatic cancers of the heart. In other embodiments, cancer cells used to source exosomes are selected based on their similarity to cells in an area to be treated, such as in heart tissue (e.g., a primary sarcoma of the heart) or epithelium (e.g., a primary carcinoma of the skin or epithelium).

In some embodiments, the cancer cell derived exosomes will contain or be enriched in compared to a corresponding non-cancerous cell, miRNA that upregulates hTERT (human Telomerase reverse transcriptase) or other kinds of miRNA associated with a cancer phenotype such as miR-451, miR-201 or miR-132 associated with reduction in apoptosis or miR-146a, miR290-295 cluster, or miR-294 associated with cell survival, cell cycle progression and cellular proliferation. The invention provides a way to temporarily increase telomerase activity in a non-cancerous target cell without inducing a detrimental overproduction of telomerase.

They may contain or be enriched in other miRNAs such as miR-22 associated with reduction in fibrosis in myocardial infarction or miR-19a associated with activation of Akt and ERK signaling pathways. Cancer cell-derived exosomes may be assayed from levels of miRNA species by methods known in the art and selected for use in therapy based on the presence (or absence) of a particular miRNA.

In some embodiments, cancer cell-derived exosomes are derived from autologous cancer cells or be fully histocompatible with a subject undergoing treatment, from cancer cells that are partially histocompatible with a subject being treated (e.g., allogenic cancer cells) or xenogeneic cancer cells. When cells are administered in conjunction with cancer cell-derived exosomes, the cells too may be autologous, partially or fully histocompatible, allogenic, or xenogeneic.

The cancer cell-derived exosomes may also be administered in conjunction with one or more biological products that promote heart growth, repair or regeneration. These include insulin-like growth factor 1, hepatocyte growth factor, or high-mobility group protein B1 which can increase cardiac stem cell migration to an area affected by myocardial infarction damage, and promote proliferation and survival of cells involved in repair or regeneration. In some embodiments, a member of the fibroblast growth factor family can be administered in conjunction with cancer cell-derived exosomes to induce cell-cycle re-entry of small cardiomyocytes. In still other embodiments, vascular endothelial growth factor may be administered in conjunction with cancer cell derived exosomes as it has been found to enhance recruitment of native cardiac cells to an infarct site and exert an angiogenic effect.

The treatment methods disclosed herein may be accompanied by drug treatment, such as by administration of a conventional drug that initiates perfusion or reduces physical exertion on the heart. These include at least one of an angiotensin converting enzyme, ACE inhibitor, benazelpril, lotensin, lotensin HCT, Lotrel, Captopril, Apo-Capto, Capoten, Capozide, Novo-Captopril, Nu-Capto, syn-Captopril, Enalapril, Lexxel, Vaseretic, Vasotec, Fosinopril, Lin-Forsinopril, Monopril, Monopril HCT, Lisinopril, Prinivil, Pinzide, Zestoretic, Zestril, Quinapril, Accupril, Accuretic, Ramipril, Altace, Ramase, aspirin, acetylsalicylic acid, NSAID, ASA, Tenormin, Warfarin, Athrombin-K, Carfin, Coumadin, PanWarfarin, Sofarin, Warnerin, Direct Formulary Aspirin, Halfprin, Novasen, Alteplase, Activase, Actilyse, Reteplase, Retavase, Streptokinase, Streptase, Tenecteplase or TNKase. Antiplatelet agents and beta blockers may be used in conjunction with the invention as well as certain biological factors such as acidic fibroblast growth factor (aFGF), basic fibroblast growth factors (bFGF), or tumor necrosis factor alpha (TNF-alpha).

Another embodiment of the invention involves a composition that includes cancer cell-derived exosomes in combination with a pharmaceutically acceptable excipient or carrier, preferably one that preserves an ability of the exosomes to merge with and release their contents into cells in or around tissue damaged by myocardial infarction. In some embodiments the cancer derived exosomes may be implanted on or in a gel, such as a gel patch or a gel strip. In other embodiments, they may be incorporated on or into a bandage, dressing wrap, self-adhesive covering, time-release covering, or other wound covering.

Generally, the exosomes in this composition are isolated or purified away from cancer cells or their non-exosomal components, such as cellular proteins and debris. The exosomes in this composition typically are suspended in or otherwise present in a pharmaceutically acceptable carrier or excipient that does not substantially contain serum or serum proteins. Preferably, the composition is sterile and kept at a temperature that preserves the ability of the exosomes to maintain their ability to merge with and release their contents into target cells including cardiomyocytes, cells or around tissue damaged by myocardial infarction, microvascular cells, vascular endothelial cells, and stem cells such as mesenchymal stem cells (e.g., from Wharton's jelly or umbilical cord blood) or adipose-derived mesenchymal stem cells.

In some embodiments, the exosomes are contacted with cells already in or around the heart, vasculature or other tissues damaged by myocardial infarction. In other embodiments, the cancer cell-derived exosomes may be contacted ex vivo or in vitro, or administered in conjunction with cells such as cardiomyocytes, vascular endothelial cells, or stem cells, such as autologous or non-autologous stem cells.

Another embodiments of the invention is directed to a method for isolating exosomes from cancer cells that includes culturing cancer cell in a medium, preferably a serum-free medium, under conditions that produce conditioned medium, separating exosomes from cancer cells and cellular debris in the conditioned medium using size exclusion chromatography (SEC), and optionally, (i) determining whether exosome-associated markers such as CD9 and HSPA8 are present in the separated exosomes and/or (ii) determining whether cell associated markers such as Grp78, PHB1 or GM130 are present in the separated exosomes; and/or determining whether cellular apoptosis marker(s) are present in the separated exosomes, and/or determining whether a cancer associated or cancer-specific antigen present in the cancer cells is present in the separated exosomes. When exosomes contain cellular markers, further purification steps may be used to remove cells or cellular debris including repeating SEC or by affinity purification using ligands that selectively bind to either cellular debris and separate them from exosomes or ligands that selectively bind to exosomes, but not to cellular debris. In some embodiments, nanoparticles are isolated from the conditioned media of grown cells. To confirm that these nanoparticles are in fact exosomes, cellular/apoptotic markers (e.g., mapkap-2) be checked. For example, if nanoparticles obtained from conditioned media contain any of these markers, they can be designated as cellular fractions and debris, not rich in or not containing released exosomes. In such a case further purification is conducted to eliminate non-exosomal cell fractions and debris.

EXAMPLES

Materials and Methods. Cell lines are obtained from a cell bank and are cultured according based on provided instructions or known culture methods for a cell line. Cell lines include triple negative breast cancer cell line [MDA-MB-231 (ATCC® HTB-26™)], colorectal cancer cell line [HT-29 (ATCC® HTB-38™)], and mesenchymal stem cell line [Bone Marrow-Derived Mesenchymal Stem Cells (ATCC® PCS-500-012™)]. In addition, AC16 human cardiomyocyte cell line (SCC109, Merck-Millipore, MA, USA) and a microvascular endothelial cell line [HMEC-1 (ATCC® CRL-3243™)] are used for functional assays purposes.

Exosome isolation. Exosomes are isolated from the conditioned media of the cultured cancer cell lines and mesenchymal stem cell line. The cells are initially cultured in a serum free media for 48 hours. Serum free media is used prior to exosome isolation in order to minimize serum proteins, mainly albumin, contamination. Condition media from the cultured cells are collected and exosomes are isolated using the size exclusion chromatography (SEC) approach. Size exclusion columns for exosomes separation are available commercially and this procedure is carried out following the manufacturer's instructions (Izon Science Ltd, Oxford, UK). Briefly, the condition media are passed through the separation column and the fraction containing the exosomes is collected.

Use of the SEC approach for exosome isolation offers several advantages including that no precipitating reagent is needed so that exosomes are free of reagent residues and because SEC can be completed in a relatively short amount of time allowing for same day isolation and use of exosomes in functional assays. For embodiments requiring sterile exosome preparations such as for in vivo work the procedures above are conducted under sterile conditions.

Exosome characterization. Exosomes are characterized using two techniques; transmission electron microscopy (TEM) for size verification, and western blotting to check protein content of the exosomes.

For TEM examination, exosomes are washed with distilled water before being fixed with 4% paraformaldehyde for 15 minutes and washed again. Then, 50%, 70% and 100% ethanol are added consecutively to remove excess water. Fixed samples are placed on an EM stub, gold sputtered and measurements and images are taken using the JEOL-1400 TEM (JEOL Ltd, Tokyo, Japan).

To conduct the western blot assay, exosomes are lysed and the total protein yield is measured using the Bradford assay. Then, the sample is mixed with a detergent to unfold the proteins before loading into the gel. The proteins are separated via electrophoresis, then transferred onto the blotting membrane. Next, a blocking reagent is added before incubating with the primary antibody, and then, the secondary antibody. Finally, the secondary antibody is detected and imaged using the ChemiDoc XRS+ system (Bio-Rad Laboratories).

During western blotting, two exosome antibody markers are checked, CD9 and HSPA8. in addition, since other cellular compartments produce extracellular vesicles, endoplasmic reticulum (Grp78 also known as BiP or HSPA5), mitochondria (PHB1), and Golgi apparatus (GM130) markers are used as negative controls. A cell apoptosis marker is included as well to verify the absence of cell debris; Van Deun J, Mestdagh P, Sormunen R, Cocquyt V, Vermaelen K, Vandesompele J, et al. The impact of disparate isolation methods for extracellular vesicles on downstream RNA profiling. J Extracell Vesicles. 2014; 3: Lasser C, Eldh M, Lotvall J. Isolation and characterization of RNA-containing exosomes. J Vis Exp. 2012(59): e3037.

All antibodies are purchased from Cell Signaling Technology (Danvers, Mass., USA), and western blot materials and buffers are purchased from Bio-Rad Laboratories (Hercules, Calif., USA). Absence of such proteins indicate that there is no contamination of other extracellular vesicle forms in the exosome preparation.

Evaluating the effect of cancer cell-derived exosomes on cardiovascular cells proliferation. A proliferation assay for both cardiomyocyte and microvascular endothelial cells is conducted using the xCELLigence real-time system (RTCA-DP version; Roche Diagnostics, Basel, Switzerland) with E-Plates 16 (Roche Diagnostics). The xCELLigence system monitors cellular events in real time, recording label-free changes in electrical impedance, which in turn are reported as cell index values. Cells suspended in medium containing cancer cell-derived or MSC-derived exosomes (0-400 µg/ml) are loaded into the E plate-16 wells ($1\times10^4$ cell per well); 45. Teng X, Chen L, Chen W, Yang J, Yang Z, Shen Z. Mesenchymal Stem Cell-Derived Exosomes Improve the Microenvironment of Infarcted Myocardium Contributing to Angiogenesis and Anti-Inflammation. Cell Physiol Biochem. 2015: 37(6): 2415-24; Zhao Y, Sun X, Cao W, Ma J, Sun L. Qian H, et al. Exosomes Derived from Human Umbilical Cord Mesenchymal Stem Cells Relieve Acute Myocardial Ischemic Injury. Stem Cells Int. 2015; 2015: 761643; O'Brien, et al., Eur J. Cancer, 2013; 49(8): 1845-59; Qu, et al., Dig. Liver Dis 2009; 41(12): 875-80; Yang, et al., Mol. Med. Rep. 20138; 40: 1272-8. Then, the E plate-16 is placed on the RTCA DP analyser and measurement is commenced for 48 hours. Cell proliferation results in an increased number of cells attaching onto the electronic sensors integrated into the bottom of the wells. This increases the electrical impedance and consequently the cell index values.

Evaluating the effect of cancer cell-derived exosomes on cardiomyocytes apoptosis. Cardiomyocytes treated with cancer cell-derived or MSC-derived exosomes are subjected to hypoxia then, a Terminal deoxynucleotidyl transferase dUTP nick end labeling (TUNEL) assay is conducted to detect a level of cell apoptosis and compare it to that of non-treated cells.

A colorimetric apoptosis detection kit (Titer TACS; R&D System, Minneapolis, Minn., USA) is used to quantify DNA damage. First, exosome treated cells and controls are seeded in a 96-well plate ($2\times10^5$ cells/well), and subjected to hypoxia (1.0% Oxygen) for 24 hours. Then, according to the manufacturer, cells are fixed with 3.7% buffered formaldehyde for 5 min before washing with phosphate buffer saline (PBS). Next, the cells are permeabilized with 100% methanol for 20 min, before washing again with PBS. Cells then are labeled according to the protocol in the Titer TACS Kit. The reaction is stopped after 30 minutes with 2 N HCl, and the absorbance is measured using a microplate reader at 450 nm. Apoptosis levels are estimated using the standard-generated standard curve.

Evaluating the effect of cancer cell-derived exosomes on endothelial cell migration. Migration assays for the microvascular endothelial cells are conducted using the xCELLigence real-time system with CIM-Plates 16 (Roche Diagnostics). First, all wells of the lower chamber are filled with serum free media. Then, cells suspended in medium containing cancer cell-derived or MSC-derived exosomes (0-400 µg/ml) are loaded into wells of the upper chamber ($1\times10^4$ cell per well). The CIM plate-16 is then connected to the RTCA DP analyser and measurement is commenced for 48 hours. Cells migrate through the microporous membrane (median pore size 8 µm) on the bottom of each well of the upper chamber, where they attach to the electronic sensors integrated on the underside of the membrane. This in turn increases the impedance and consequently the cell index values.

Evaluating the effect of cancer cell-derived exosomes on aortic ring sprouting. As described by Nicosia and Ottinetti, the mouse aortic ring model is a quantitative assay for the study of angiogenesis under defined culture conditions; Nicosia R F, Ottinetti A. Growth of microvessels in serum-free matrix culture of rat aorta. A quantitative assay of angiogenesis in vitro. Lab Invest. 1990; 63(1): 115-22. This ex vivo angiogenic model, where vessels grow from a segment of the aorta, reflects the complexities of angiogenesis, in that it analysis all of the key steps in this complex process. This assay investigates endothelial cell proliferation, migration, tube formation then microvessel branching. In addition, this assay investigates perivascular recruitment and remodeling, providing a comprehensive picture of the efficacy of cancer cell derived-exosomes as a pro-angiogenic factor compared with traditional cell-based assays.

Briefly, mouse thoracic aorta is excised, cleaned and cut into rings, approximately 1 mm in length, then serum-starved overnight. The next day, Individual rings are embedded in a matrix (Collagen I Rat Protein, Tail, Thermo fisher Scientific, MA, USA) in a 48-well plate. Once embedded, the rings are fed every 2 to 3 days with growth medium containing cancer cell-derived or MSC-derived exosomes. Sprouting is observed under the microscope over a period of 6 to 12 days. The number and length of sprouts are counted via confocal microscopy, and compared for the test and the control in at least 6 experimental repeats; Bellacen K, Lewis E C. Aortic ring assay. J Vis Exp. 2009(33); Masson V V, Devy L, Grignet-Debrus C, Bernt S, Bajou K, Blacher S, et al. Mouse Aortic Ring Assay: A New Approach of the Molecular Genetics of Angiogenesis. Biol Proced Online. 2002; 4: 24-31.

In vitro evaluation of tumorigenic transformation of exosome-treated cells using colony formation in soft agar assay. Anchorage-independent growth by colony formation in soft agar is used as a guide to determine cell transformation in vitro. Cardiomyocytes and endothelial cells are treated with cancer cell-derived exosomes or MSC-derived exosomes prior to conducting the assay, then observed for colony formation. In a 6-well plate, a 1.5 ml base agar layer is made of 1:1 mixture of medium containing 20% FBS and 1.5% ultra-pure low melting point (LMP) agarose (Life Technologies, CA, USA). The layer is solidified at 4° C. and warmed to 37° C. at least 15 minutes prior to the addition of the top layer. The top layer solution is 1 ml of an equal volume-mixture of 2× D-MEM medium containing 20% FBS, 1.2% LMP agarose and 0.1-0.5×105 Pre-treated cells in single cell suspension (achieved by passing cells through a 40-μm cell strainer). After being solidified at 4° C., the cell is incubated at 37° C. for 2-4 weeks. Colonies are visualized using the EVOS XL imaging system (Life Technologies) and counted using ImageJ software (89). Cells are plated in duplicate for each experiment, and each experiment is done in triplicate.

In vivo evaluation of tumorigenic transformation of exosome-treated cells. All animal work is performed in accordance with the Animal Care's Guidelines for the KAIMRC Animal Care Committee. Exosome-treated cells ($1 \times 10^7$ in 500 μL PBS) are injected subcutaneously (s.c.) in 8-week-old SCID mice (The Jackson Laboratory, ME, USA). Animals are monitored until humane endpoint (including but not limited to; >15% weight gain, abdominal distension and a sizable tumor appearance). If any tumor formed, then tumor burden is measured and compared. Also, tumors are fixed in 10% buffered formalin for 24 hours, paraffin embedded and sectioned at 5 μm for histological analysis using hematoxylin and eosin (H&E) and Ki-67 staining. If no tumors appear, animals are sacrificed humanely after six months. Animals with MI and those being treated with exosomes are monitored carefully for cancer progression. H&E and Ki-67 staining is used in the MI animal models as a confirmation tool.

Measurement of hTERT mRNA levels in cancer cell-derived and MSC-derived exosomes. Quantitative Polymerase Chain Reaction (qPCR) is used to measure the amount of hTERT mRNA in cancer cell-derived and MSC-derived exosomes. First, RNAs within the exosomes will be extracted using the miRCURY™ RNA Isolation Kit—Cell & Plant (Qiagen, Venlo, Netherlands). This kit is used for small RNA extraction from condition media-derived exosomes. Extraction is conducted following manufacture instructions, briefly, exosomes are lysed then homogenized by passing the lysate through an 18-20 gauge needle. 70% ethanol is added to the homogenized lysate, and mix thoroughly, before applying the sample to the provided column. The column is then washed a few times with the provided washing buffer. To elute, the column is transferred to a new collection tube, elution buffer is added, and centrifuged. Then, High-Capacity cDNA Reverse Transcription Kit (Thermo Fisher Scientific) are used to reverse transcript the extracted RAN into complementary DNA (cDNA). Finally, the expression of the hTERT gene is measured by q-PCR using QuantiTect SYBR® Green PCR Kit (Qiagen), and custom made TaqMan primers (Thermo Fisher Scientific). Master mix is prepared using reagent provided by the kit and the generated cDNA, then the mix is added to each well of the 96 well PCR plate, along with the appropriate primer. The plate is placed in the BIORAD CFX96 Real-Time PCR System with C1000™ thermal cycler (Bio-Rad Laboratories), and data are collected and analyzed upon cycle completion.

MicroRNA screening of cancer cell-derived and MSC-derived exosome content. Following RNA extraction as described above, single-stranded cDNAs are synthesized from all samples using the TaqMan MicroRNA Reverse Transcription Kit and the Megaplex™ RT Primers (Thermo Fischer Scientific). The reverse transcription product is pre-amplified using Megaplex™ RT Primers, Human Pool A v2.1, which contains RT primers for 377 unique microRNAs and 4 controls. The pre-amplified product is diluted using TE buffer (pH8) and then used to run real-time polymerase chain reaction (PCR) using TaqMan Universal PCR Master Mix, No AmpErase UNG on TaqMan MicroRNA Array, as described in the Applied Biosystems TaqMan® Array User Bulletin (PN 4371129).

TRAP assay for telomerase activity of cardiovascular cells, following cancer cell-derived exosomes treatment. Telomerase activity of cells treated with cancer cell-derived exosomes is measured using the Human Telomerase Reverse Transcriptase (hTERT) ELISA Quantitation Kit (Genway Biotech, San Diego, Calif., USA). According to the manufacturer's instructions, cells are lysed and the protein concentration should be measured by a Bradford assay. Then, standards, controls and samples are loaded into the hTERT pre-coated plastic microwell strip, and incubated for 1 hour at room temperature before washing with wash buffer. Detection antibody is added next, and incubated for another hour to complete the antibody sandwich. Following incubation, the wells are washed to remove any unbound detection antibody before adding streptavidin-HRP. The wells are washed again, to remove excess streptavidin-HRP then incubated with tetramethylbenzidine (TMB) substrate solution for 20 minutes, before adding the stop solution. Finally, the plate is red using a microplate reader at a wavelength of 450 nm, the intensity of the color is directly proportional to the concentration of hTERT in the sample. hTERT levels are estimated using the standard-generated standard curve.

Evaluating the cardio-protective effect of cancer cell-derived exosomes in vivo using a MI animal model. All animal work is conducted by trained veterinary surgeons at King Saud University, College of Medicine, Experimental Surgery and Animal Laboratory, in accordance with the ethical committee rules and regulations. To induce myocardial infarction, first, a healthy SD male rat is anesthetized by inhalation or injection of anesthetics, then fixed in the supine position. Second, the rat is intubated and ventilated. Third, the heart is exposed through an incision on the left-fourth intercostal space. Fourth, a suture is tied around the left coronary artery, 2-3 mm from its origin, on the left ventricular anterior wall. Infarction is verified by observing discoloration, which indicates interruption of blood flow; Kumar M, Kasala E R, Bodduluru L N, Dahiya V, Sharma D, Kumar V, et al. Animal models of myocardial infarction: Mainstay in clinical translation. Regul Toxicol Pharmacol. 2016; 76: 221-30.; Camacho P, Fan H, Liu Z, He J Q. Small mammalian animal models of heart disease. Am J Cardiovasc Dis. 2016; 6(3): 70-80.

After 60 minutes of ligation, the viable myocardial tissue bordering the infract size is injected at 3 different sites. Rats are injected with a total of 150 μl of PBS, cancer cell-derived exosomes suspension or MSC-derived exosomes suspension. Finally, the chest cavity is closed, the endotracheal tube is removed, and the rat is allowed to recover in a heated chamber; Reichert K, Colantuono B, McCormack I, Rodrigues F, Pavlov V, Abid M R. Murine Left Anterior Descending (LAD) Coronary Artery Ligation: An Improved and Simplified Model for Myocardial Infarction. J Vis Exp. 2017(122); Ovsepyan A A, Panchenkov D N, Prokhortchouk E B, Telegin G B, Zhigalova N A, Golubev E P, et al. Modeling myocardial infarction in mice: methodology, monitoring, pathomorphology. Acta Naturae. 2011; 3(1): 107-15.

A minimum of 12 rats per group is operated. Groups include Group 1: Rats injected with triple negative breast cancer-derived exosomes, Group 2: Rats injected with colorectal cancer-derived exosomes, Group 3: Rats injected with MSC-derived exosomes, and Group 4: Rats injected with PBS). A minimum total of 48 rats is used in this study; Arslan F, Lai R C, Smeets M B, Akeroyd L, Choo A, Aguor E N, et al. Mesenchymal stem cell-derived exosomes increase ATP levels, decrease oxidative stress and activate PI3K/Akt pathway to enhance myocardial viability and prevent adverse remodeling after myocardial ischemia/reperfusion injury. Stem Cell Res. 2013; 10(3): 301-12 .; Klocke R, Tian W, Kuhlmann M T, Nikol S. Surgical animal models of heart failure related to coronary heart disease. Cardiovasc Res. 2007; 74(1): 29-38.

To monitor and evaluate cardiac function and cardiovascular tissue throughout the in vivo work the following assays are carried out.

Functional assessment by echocardiography. 24 hours and 4 weeks after MI induction, two-dimensional and M-mode echocardiography are performed through the parasternal short axis using a 6-MHz transducer (ACUSON Sequoia 512 Ultrasound System Transducers, Siemens medical, Erlangen, Germany). The index of the detection includes end-diastolic volume (EDV), end-systolic volume (ESV) and left ventricular ejection fraction (LVEF). All measurements are averaged on 5 consecutive cardiac cycles and performed blindly to the animal groups by an experienced echocardiographer.

Complete blood count and biochemical analysis: 24 hours and 4 weeks after MI induction, blood is collected from the tail vein of rats. A complete blood count (CBC) is conducted, and general biochemical markers (SGPT, SGOT, creatinin and urea) is measured. In addition, two myocardial infarction-related markers, creatine kinase MB (CK-MB) isoenzyme and high-sensitivity troponin I (hs-TnI), are measured as well; Shebuski R J. Utility of point-of-care diagnostic testing in patients with chest pain and suspected acute myocardial infarction. Curr Opin Pharmacol. 2002; 2(2): 160-4. Parasuraman S, Raveendran R, Kesavan R. Blood sample collection in small laboratory animals J Pharmacol Pharmacother. 2010; 1(2): 87-93.

Histopathological evaluation. Infarction size or area-at-risk (AAR) is determined by Masson's trichrome staining (HT15 Trichrome Stain kit, Sigma, MO, USA). Hearts are collected 4 weeks post MI, washed with normal physiologic saline and fixed with 4% paraformaldehyde. The hearts are then dehydrated in gradual ethanol series before being embedded in paraffin and cut into 8 µm sections, For each sample, 5 sections are examined. The borders of the infracted area are defined and calculated via Image J image analysis software; Schneider C A, Rasband W S, Eliceiri K W. NIH Image to ImageJ: 25 years of image analysis. Nat Methods. 2012; 9(7): 671-5.

For histological evaluation of tissue damage, cardiac tissue is stained with H&E. Hearts are collected 4 weeks post MI, washed with normal physiologic saline, and the ventricles are dissected from the atria, large vessels, and connective tissues. The collected samples are fixed with 4% paraformaldehyde, dehydrated in gradual ethanol series, then embedded in paraffin and cut into 4 µm sections. The pathologist does not know which group each slide is corresponded to. The findings are classified into the following degrees, in order to compose a range of histologic myocardial injury: (0) No change: (1) Mild—focal myocyte damage or small multifocal degeneration with slight degree of inflammation, (2) Moderate—extensive myofibrillar degeneration and/or diffuse inflammatory process, (3) Severe—necrosis with diffuse inflammatory process. In vivo cardiac cell proliferation assay by 5-ethynyl-2'-deoxyuridine (EdU): Click-iT™ EdU cell proliferation Assay Kit (Cat #C10339, Invitrogen, CA, USA) is used to examine in vivo cell proliferation, 4 weeks post-MI. EdU (Sigma) is injected at a dose of 50 mg/kg body weight in a solution of 10 mg/ml PBS (pH 7.35); Hsu T L, Hanson S R, Kishikawa K, Wang S K, Sawa M, Wong C H. Alkynyl sugar analogs for the labeling and visualization of glycoconjugates in cells. Proc Natl Acad Sci U S A. 2007; 104(8): 2614-9.

For each animal group (Group 1: Rats injected with triple negative breast cancer-derived exosomes, Group 2: Rats injected with colorectal cancer-derived exosomes or Group 3: Rats injected with MSC-derived exosomes, Group 4: Rats injected with PBS), the animals will receive an intraperitoneal injection of EdU, then each group is subdivided into 2 groups. In group A, animals (n=6) are sacrificed at 1 h after injection. Whereas animals in group B (n=6) are sacrificed at 2 h after injection. Hearts of every group are harvested and cryopreserved in OCT medium (Sigma). The frozen hearts are then sectioned at 6 µm with a cryostat, and random 12 sections of each heart are stained using the Click-iT™ EdU imaging kit manufacturer protocol. Briefly, following fixation, the tissue sections are incubated with a Click-iT™ reaction cocktail for 30 minutes. Then, the section are washed with 3% BSA in PBS. Finally, the sections are examined using a fluorescence microscope.

Double staining of EdU and cardiac cell molecular and angiogenic markers. Following the EdU staining described above, sections are double stained using the following antibodies; cardiac transcription factors: goat anti-Nkx2.5 [Homeobox protein Nikx-2.5, SC-8697 1:150 (Santa Cruz Biotechnology, CA, USA)] and goat anti-Gata 4 [SC-1237, 1:200 (Santa Cruz Biotechnology)], specific marker of cardiomyocytes: mouse anti-TnT [Trinitrotoluene, 1:1,000 (Thermo Scientific)], endothelial cell marker: mouse anti-CD31 [cluster of differentiation 31, 1:500 (BD Pharmingen, CA, USA)], vascular smooth muscle marker: rabbit anti-SMM IgG [smooth muscle myosin, BTI-562, 1:300 (Biomedical Technologies, MA, USA)], angiogenesis markers: mouse anti-CD34 [cluster of differentiation 34, 1:50-1:500 (ThermoFisher)], rat anti-VEGF [vascular endothelial growth factor, 1:20-1:100 (ThermoFisher)] and rat anti-hypoxia-inducible factor 1-α [HIF1-α, 1:20-1:50 (ThermoFisher)]. The sections are incubated with the primary antibody at 4° C. overnight or at 37° C. for 1 h. Then the sections are washed and incubated with the appropriate secondary antibody. Finally the stained sections are examined using a fluorescence microscope.

Statistical analysis. Data analysis is performed with Minitab 17 [Minitab 17 Statistical Software (2010). State College, Pa.: Minitab, Inc. (www.minitab.com)]. Statistical significance is defined as $p<0.05$, and determined by a paired t statistical test or by an ANOVA general linear model statistical test, followed by Tukey's HSD pairwise comparisons. A minimum of three separate repeats are conducted for each set of experiments.

The Examples above help describe the advantages of using cancer cell derived exosomes compared to exosomes from non-cancerous cells for treatment of myocardial infarction. These advantages include improved left ventricular function, improved myocardial perfusion and reduction in collagen scar formation leading to a better quality of life for a patient.

Terminology. Terminology used herein is for the purpose of describing particular embodiments only and is not intended to be limiting of the invention.

The headings (such as "Background" and "Summary") and sub-headings used herein are intended only for general organization of topics within the present invention, and not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms, may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under, The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the, specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for repairing or regenerating tissue damaged by myocardial infarction in a subject comprising: administering to the subject in need thereof an effective amount of cancer cell-derived exosomes; wherein the cancer cell-derived exosomes are administered in an effective dosage subcutaneously, intravenously, or into or around scar tissue or other tissue damaged by myocardial infarction.

2. The method of claim 1, wherein the tissue damaged by myocardial infarction comprises a zone of ischemia containing cells that can regain function after the onset of the myocardial infarction.

3. The method of claim 1, wherein the tissue damaged by myocardial infarction comprises an area of injury containing cells that can regain function after the onset of the myocardial infarction.

4. The method of claim 1, wherein the tissue damaged by myocardial infarction comprises an area of infarction containing dead cells or necrotic tissue exhibiting myofibrillar degeneration and/or diffuse inflammatory processes.

5. The method of claim 1, wherein the tissue damaged by myocardial infarction comprises an area of incomplete scar formation or wherein the subject has had a myocardial infarction within the last three months.

6. The method of claim 1, wherein the tissue damaged by myocardial infarction comprises a collagen scar.

7. The method of claim 1, wherein the tissue damaged by myocardial infarction is located in the left ventricle.

8. The method of claim 1, wherein the cancer cell-derived exosomes are obtained from breast cancer cells which may be obtained from a subject, from cancer cells cultured in vitro, or from a recognized or certified cancer cell line.

9. The method of claim 1, wherein the cancer cell-derived exosomes are obtained from colorectal cancer cells.

10. The method of claim 1, wherein the cancer cell-derived exosomes are obtained from a cancer of mesenchymal origin.

11. The method of claim 1, wherein the cancer cell-derived exosomes contain miRNA that upregulates hTERT (human Telomerase reverse transcriptase).

12. The method of claim 1, further comprising administering autologous or non-autologous stem cells.

13. The method of claim 1, further comprising administering a drug that initiates perfusion or reduces physical exertion on the heart.

14. The method of claim 1, wherein the cancer cell-derived exosomes are administered into or around scar tissue or other tissue damaged by myocardial infarction in an effective dosage ranging from about 0.01 to 3,000 µg of exosome protein per kg of body weight of the subject.

15. The method of claim 1, wherein the cancer cell-derived exosomes are administered intravenously or subcutaneously in an effective dosage ranging from about 0.01 to 3,000 µg of exosome protein per kg of body weight of the subject.

* * * * *